United States Patent [19]

Kaster

[11] 4,319,364
[45] Mar. 16, 1982

[54] PIVOTING DISC HEART VALVE

[75] Inventor: Robert L. Kaster, 2730 Vagabond La., Plymouth, Minn. 55447

[73] Assignee: Robert L. Kaster, Plymouth, Minn.

[21] Appl. No.: 87,917

[22] Filed: Oct. 24, 1979

[51] Int. Cl.³ .............................................. A61F 1/22
[52] U.S. Cl. ...................................... 3/1.5; 137/527.8
[58] Field of Search .................. 3/1.5; 137/512.1, 527, 137/527.8

[56] References Cited

U.S. PATENT DOCUMENTS

| 3,825,956 | 7/1974 | Child | 3/1.5 |
| 3,825,957 | 7/1974 | Kaster | 3/1.5 |
| 3,959,827 | 6/1976 | Kaster | 3/1.5 |
| 4,021,863 | 5/1977 | Woien | 3/1.5 |

Primary Examiner—Clifford D. Crowder
Attorney, Agent, or Firm—Joseph F. Breimayer; Carl A. Forest

[57] ABSTRACT

Heart valve including an annular valve body having an inner wall defining a blood flow passage, a guide strut including an integral pivot surface extending radially inward of the valve body and a disc occluder having a central aperture engaged over the disc guide strut, a disc stop extending radially inward of the valve body opposite the guide strut, and pivot projections extending radially inward of the valve body and equally spaced from the guide strut whereby the disc pivots between occluding and non-occluding surfaces in response to downstream blood pressure gradients across the disc.

12 Claims, 7 Drawing Figures

PIVOTING DISC HEART VALVE

BACKGROUND OF THE INVENTION

1. Field of the Invention

The present invention relates generally to artificial body members, and more importantly, pertains to a pivoting disc heart valve.

2. Description of the Prior Art

The replacement of damaged or diseased natural heart valves with mechanical heart valves has become medically quite common. Of the various mechanical heart valve designs which have been proposed, pivoting disc valves of the type disclosed, for example, in U.S. Pat. Nos. 3,825,957 and 4,021,863, have the significant feature of providing minimal interference to blood flow through the heart valve. The valves of the two abovementioned patents each employ a pivoting disc having a center hole and a guide strut which extends through the center hole guiding the disc between its open and closed positions. The valves include a generally annular valve body having various inwardly directed projections arising from its inner surface where the projections act as pivot surfaces urging the disc to pivot between open and closed positions in response to cyclic blood pressure differentials across the valve. The manufacture of the valves such as those described in the above-mentioned patents is a meticulous process which involves machining and polishing the valve body and associated disc-supporting structure to exacting tolerances.

Heart valves should disturb blood flow as little as possible. The orifice of the heart valve should be as free as possible of internal projections disturbing the blood flow. It is particularly important from the standpoint of blood flow dynamics that the heart valve be as free as possible of obstructions immediately upstream from the orifice of the heart valve. On the other hand, in order to avoid interference with the heart valve operation from encroaching heart tissue downstream of the heart valve, the heart valve should further be as free as possible of physical structure extending downstream from the heart valve. Finally, the heart valve must be structurally strong, and be physically capable of reliable operation in opening and closing through millions of cycles.

The pivoting disc heart valve of the present invention incorporates a pivot integrally onto a central guide strut. The guide strut provides for positive retention of a radiopaque occluder, and simplifies manufacture.

SUMMARY OF THE INVENTION

The present invention provides a pivoting disc heart valve including radially inward disc supporting projections and having physical structure stability.

According to one embodiment of the present invention, there is provided a pivoting disc heart valve including an annular valve body having an interior wall providing a circular passage for blood flow through the valve and an exterior circumferential groove around the body accepting a rotatable knitted surgical sewing ring, an integral pivoting single disc occluder, guide strut member extending radially inward of the valve body and including a rounded pivot surface, disc guide portion, a pivot open stop surface, an upstream facing surface, and a U-shaped internal rounded surface, a closed disc stop having a downstream facing surface extending radially inward of the valve body opposite the guide strut, two pivot projections extending radially inward of the valve body equally spaced from the guide strut and having downstream facing disc stop surfaces and pivot-open stop surfaces, and a radiopaque disc occluder having a central aperture positioned over the guide strut whereby the disc pivots about the rounded pivot surface of the guide strut in response to the blood pressure gradients across the heart valve thereby engaging on the respective surfaces of the guide strut and pivot projections in an open position and on the pivot projections and disc stop in a closed position.

One significant aspect and feature of the present invention is a disc guide strut having a disc guide portion which generally extends coaxially with the blood flow passage of the valve body thereby resulting in minimal turbulence to the blood flow. The guide strut includes an upstream facing pivot surface adjacent to the central aperture of the disc that causes the disc to pivot open in response to pressure gradients across the heart valve. The central aperture of the disc engages around a disc guide portion of the guide strut. The central aperture of the disc translates about a U-shaped portion between the pivot surface and the disc guide portion of the guide strut.

In the open position, the disc of the heart valve is centrally located within the valve orifice, thereby improving hemodynamic efficiency, reduced flow resistance, increased effective valve orifice area, and reduction of flow stasis on the outflow side of the disc.

The physical structure of the heart valve is low in profile, without outer perimeter projecting structures that avoid encroachment or impingement upon annular tissue. The structure is open-membered, where all members project centrally without distal attachments.

One piece construction is achieved by machining a solid piece of metal into the final configuration with an absence of bends, welds or joints. This construction preserves the original molecular integrity of the metal thereby insuring long term structural integrity.

BRIEF DESCRIPTION OF THE DRAWINGS

Other objects and many of the attendant advantages of this invention will be readily appreciated as the same becomes better understood by reference to the following detailed description when considered in connection with the accompanying drawings, in which like reference numerals designate like parts throughout the FIGURES thereof and wherein.

DESCRIPTION OF THE PREFERRED EMBODIMENT

Figure 1:
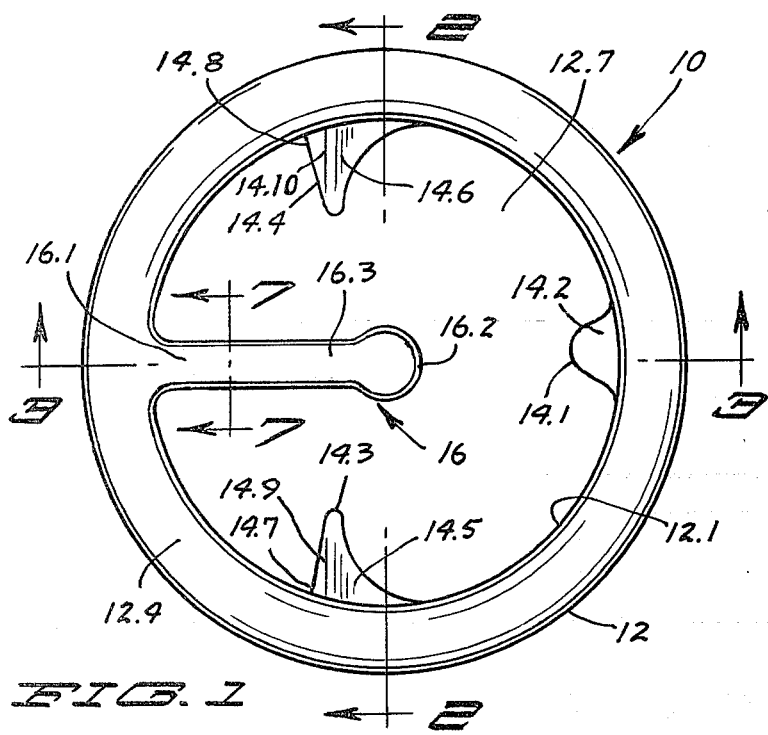
FIG. 1 is a plan view of the heart valve of the present invention with the disc removed for purposes of clarity in illustration and explanation.
Figure 2:
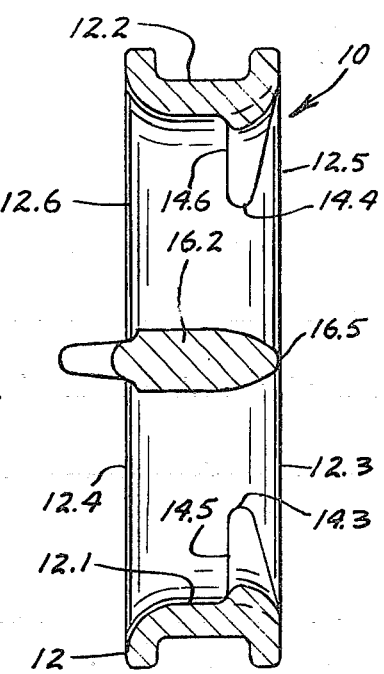
FIG. 2 is a cross-sectional view taken along line 2—2 of FIG. 1.
Figure 3:
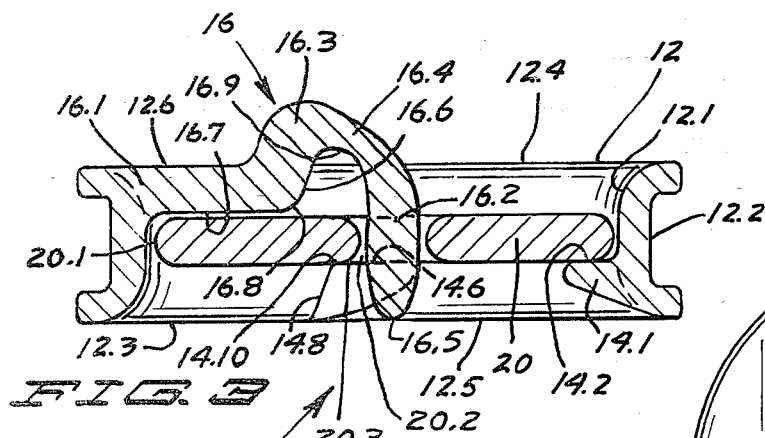
FIG. 3 is a cross-sectional view taken along line 3—3 of FIG. 1 showing the disc in a closed position.

FIG. 1, which illustrates a plan view of a pivoting disc heart valve 10 of the present invention with a single disc occluder 20 removed fro purposes of clarity in illustration and explanation, shows an annular valve body 12. FIG. 2 illustrates a cross-sectional view taken along line 2—2 of FIG. 1. The annular valve body 12 includes a smoothly rounded interior wall 12.1 having outwardly diverging valve body inflow and outflow edges 12.3 and 12.4 respectively defining aa bell-shaped inflow side 12.5 and a bell-shaped outflow side 12.6 as illustrated in FIG. 3. The interior wall 12.1 defines a generally circular blood flow passage 12.7 through the valve body 12. A circumferential groove 12.2 as illustrated in FIG. 3 recesses into and around the exterior surface of the annular valve body 12 and accepts a rotatable knitted surgical sewing ring for surgical fixation of the heart valve 10 to a valve orifice within the heart. A closed position disc stop 14.1 projects inwardly from the inner wall 12.1 of the annular valve body 12 adjacent to the inflow edge 12.3. A downstream facing surface 14.2 is provided on the disc stop 14.1 against which a pivoting single disc occluder 20 as later described seats when the disc 20 is in a closed flow occluding position as illustrated in FIG. 3. A pair of opposing pivot projections 14.3 aand 14.4 project inwardly along a chord from the inner wall 12.1 of the annular valve body 12 adjacent to the inflow edge 12.3 and are equally spaced from the disc stop 14.1. The pivot projections 14.3 and 14.4 include downstream facing disc stop surfaces 14.5 and 14.6 which together with the surface 14.2 of the disc stop 14.1 define a plane parallel to the plane of the annular valve body 12 and are positioned below the mid-plane of the valve body 12 by a distance substantially approximating one-half the thickness of the disc 20. The pivot projections 14.3 aand 14.4 include coplanar pivot-open stop surfaces 14.7 and 14.8 extending generally in an upstream direction at an oblique angle to the disc stop surfaces 14.5 and 14.6 respectively. The junctions of the pivot-open stop surface 14.7 and 14.8 with the respective disc stop surfaces 14.5 and 14.6 provide rounded pivot surfaces 14.9 and 14.10. The pivot surfaces 14.9 and 14.10 are in line and lie along a chordal axis of the annular body 12 opposite the disc stop 14.1.

FIG. 2 illustrates a cross-sectional view taken along line 2—2 of FIG. 1 where all numerals correspond to those elements previously delineated.

Figure 5:
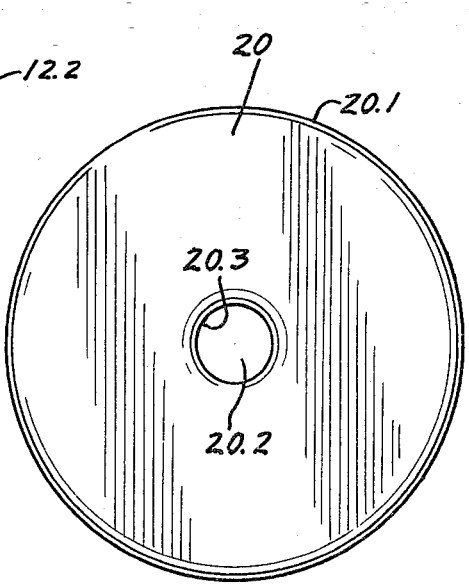
FIG. 5 is a plan view of the disc shown in FIGS. 3 and 4.
Figure 4:
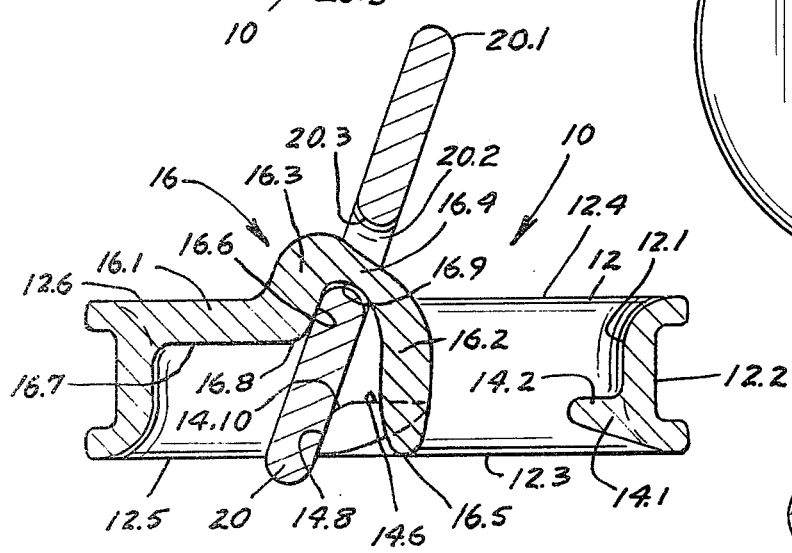
FIG. 4 is a cross-sectional view similar to FIG. 3 showing the disc in an open position.
Figures 6, 7:
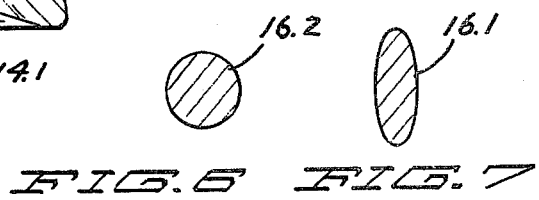
FIG. 6 represents a partial cross-section of a coaxial upstream extending portion of a disc guide.
FIG. 7 represents a partial cross section taken along line 7—7 of FIG. 1.

FIG. 3, which illustrates a cross-sectional view taken along line 3—3 of FIG. 1, shows the disc 20 as later described in a closed position in the heart valve 10. An integral pivoting single disc occluder guide strut 16 arises from the rounded interior wall 12.1 of the annular valve body opposite the disc stop 14.1 and projects radially inward of the valve body 12 as illustrated by the numeral 16.1. After traversing radially inwardly approximately one-third of the inner diameter of the annular valve body 12, the strut 16 turns in a generally downstream direction as illustrated by the numeral 16.3, then abruptly turns upstream, and terminates in a disc guide 16.2 including an end 16.5. The disc guide 16.2 is coaxial with the flow passage 12.7 and has a circular cross-section as illustrated in FIG. 6 slightly smaller in diameter than a central aperture 20.2 of the disc 20. A cross member 16.4 joins the downstream extending portion 16.3 and the coaxial, upstream extending disc guide 16.2 of the strut 16. The cross member 16.4 is of substantially reduced cross-sectional diameter with respect to the central aperture 20.2 of the disc 20. The radially inward projecting portion 16.1 of the strut 16 is generally elliptical in cross-section as illustrated in FIG. 7, and has the maximum dimension parallel to the direction of blood flow thereby reducing turbulence. The configuration of the strut 16 is cross-section becomes more gently rounded in the section 16.4 to the free-ended, coaxial upstream extending portion 16.2 of the strut 16 which is circular is cross-section. Thus, in reference to FIG. 7, the surfaces 16.6 and 16.7 and the pivot surface 16.8 are narrow surfaces that provide line contact with the downstream surface of disc 20 when these surfaces are brought into contact during the pivoting open operation of the disc (to be described below). The end 16.5 of the coaxial strut portion is a rounded tapered tip, and extends completely through the central orifice of the disc 20 when the latter is in the closed position as illustrated in FIG. 3. A single disc occluder 20, as also illustrated in FIGS. 3, 4 and 5, includes a circular outer periphery 20.1 and a central aperture 20.2 having a rounded interior wall 20.3 which is guided by disc guide 16.2 and retained in the open position by cross member 16.4. The diameter of the disc 20 is slightly less than the internal diameter of the blood flow passage 12.7.

FIG. 4, which illustrates a cross-sectional view similar to FIG. 3 showing the disc 20 in an open position, shows a pivot open stop narrow surface 16.6 on the downstream extending portion 16.3 of the strut 16. The pivot open stop narrow surface 16.6 is generally parallel to the plane defined by the pivot-open stop surfaces 14.7 and 14.8 of the respective pivot projections 14.3 and 14.4, and is positioned from the plane by a distance substantially equal to the thickness of the disc 20. The strut narrow surface 16.6 merges into a substantially upstream-facing, rounded surface 16.7 of the inwardly extending strut portion 16.1 at the rounded upper surface 16.8. The pivot surface edge 16.8 is positioned to engage the disc 20 exteriorly of the central aperture 20.2 as illustrated in FIGS. 3 and 4. The upstream-facing surface 16.7 of the strut 16 is spaced in the direction of blood flow from the plane defined by the downstream-facing disc stop surfaces 14.5, 14.6, and 14.2 by a distance slightly greater than the thickness of the disc 20. U-shaped rounded internal surface 16.9 defined by mutually confronting surfaces of the strut 16 as the strut 16 undergoes downstream and then upstream changes in direction is sufficiently large so as to accommodate the disc 20 when the disc 20 is in an open position as illustrated in FIG. 4.

Preferred Mode of Operation

The valve body 12 including the disc stop 14.1, pivots projections 14.3 and 14.4, and disc guide strut 16 are preferably machined as an integral unit from a single piece of solid metal such as titanium and has no welds or introduced bends. The valve body 12 is open-membered in which all members project centrally without distal attachment, the blood contacting surfaces of the valve 10 are substantially polished to a mirror finish. The disc 20 can be formed from a pyrolized carbon material such as Pyrolite, a product of Carbomedics, Inc.

The disc 20 is installed in the valve body 12 from the upstream side of the valve body 12 by tilting the disc 20 so tht a portion of the peripheral edge is downstream from the disc stop 14.1 and from one of the pivot projections such as 14.4 and the tip 16.5 of the strut 16 is received in the central aperture 20.2 of the disc 20. The coaxial portion 16.2 of the strut 16 is then urged resiliently toward the pivot projection 14.4 until the edge of the disc 20 clears the opposing pivot projection 14.3. The strut 16 then springs back and forceably adjusted as necessary to align member 16.2 coaxially with 12.7 to the original position as shown in FIG. 2. The disc 20 is retained in the valve body 12 by the strut 16 and the respective surface extending radially inward from the interior wall 12.1.

When the heart valve 10 is closed as illustrated in FIG. 3, the disc 20 is seated on the downstream-facing surface 14.2 of the disc stop 14.1 and on the downstream-facing surfaces, 14.5 and 14.6 of the pivot projections 14.3 14.4 respectively thereby being supported in a plane parallel to the plane of the annular valve body 12. Non-appreciable contact of the peripheral edge of the disc 20 with the orifice wall 12.1 occurs because the diameter of the disc is less than that of the valve orifice.

As the pressure of blood upstream of the heart valve 10 increases, the disc 20 is moved so that the downstream-facing surface of the disc 20 comes into contact with the surface 16.7 of the inwardly projecting portion 16.1 of the guide strut 16. The disc 20 is then pivotally forced about the rounded pivot surface 16.8 of the guide strut 16 by the pressure gradient of the blood flow. During pivoting, the internal surface 20.3 of the central aperture 20.2 glides around and does not come into contact with the coaxial portion 16.2 of the guide strut 16. During the latter phase of the pivoting open event, the inner surface of the central aperture 20.2 of the disc is caused to slide along the confronting surface 16.9 of the guide strut 16. Concurrently, the downstream-facing surface of the disc 20 adjacent the central aperture 20.2 continuously engages the rounded pivot surface 16.8 in a combined pivoting and sliding motion as the disc 20 pivots toward an open position. As the pivoting action of the disc 20 continues to the open position, the disc 20 moves in a downstream direction a small distance as permitted by the reduced diameter of the cross member 16.4 of the guide strut 16.

When the disc is in a fully open position as illustrated in FIG. 4, the disc 20 is at an angle of about 70°–75° plus or minus two degrees to the plane of the annular valve body 12 and is supported by the pivot stop surfaces 14.7 and 14.8 of the pivot projections 14.3 and 14.4, by the inner surface 16.6 of the downstream-extending portion 16.3 of the guide strut 16, and by the reduced diameter of the cross member 16.4 of the guide strut 16. The cross member 16.4 captures the disc 20 downstream in the heart valve 10. The diameter of the cross member 16.4 is significantly less than the diameter of the central aperture 20.2 of the disc 20 to permit the disc 20 to translate in a generally upstream and downstream directions when the disc 20 is in the open non-occluding position. The diameter of the cross member 16.4 is preferably not greater than about two-thirds of the diameter of the central aperture 20.2 and can be as small as one-half the central aperture diameter. The surfaces 14.7, 14.8 and narrow surface 16.6 limit the opening of the disc 20. The disc 20 is retained in the position of FIG. 4 until the surge of blood through the heart valve 10 ceases.

The closing event of the disc 20 commences when the upstream pressure exceeds the downstream pressure, and blood begins to flow back through the heart valve 10 in an upstream direction. The upstream flow of blood causes the disc 20 initially to translate in an upstream direction until its peripheral edges contact the inner walls of the valve body 10 adjacent to the pivot projections 14.3 and 14.4. Continued upstream blood flow causes the disc to pivot about the aligned pivot surfaces 14.9 and 14.10. The periphery of the disc 20 is supported by sliding along the interior wall 12.1. As the disc 16 approaches the closed, flow-occluding position, the upstream surface of disc 20 approaches the surface 14.2 of the disc stop 14.1 while the opposite surface of the disc 20 approaches surface 16.7 of the inwardly projecting portion 16.1 of the disc guide strut 16. The disc 20 finally seats in the closed position against the downstream-facing sufaces 14.2, 14.5 and 14.6 of the disc stop and pivots projections 14.1, 14.3 and 14.4 respectively.

Various modifications can be made to the heart valve of the present invention without departing from the apparent scope of the present invention.

Having thus described the invention, there is claimed as new and desired to be secured by Letters Patent:

1. A prosthetic heart valve comprising:
an annular valve body including an inner wall and a substantially circular blood flow passage therethrough; a disc occluder including a central aperture and pivotable between occluding and non-occluding positions in said blood flow passage; disc guide strut means extending substantially radially inward from said valve body and including a U-shaped portion extending first downstream and then upstream, through said central aperture of said disc occluder and terminating in a disc guide extending upstream coaxially with said blood flow passage; said disc guide strut means including cross member means for limiting downstream movement of said disc occluder from said valve body and integral pivot means, said pivot means including an upstream facing surface means extending parallel with the plane of said valve body and the plane of said disc occluder in its occluding position and a pivot open stop means for engaging with said disc occluder in its non-occluding position; aand further opposing pivot projections projecting inwardly along a chord from said inner wall of said annular valve body and including downstream facing closed position disc stop surfaces; whereby said disc occluder pivots to an occluding position in response to an upstream pressure gradient across said heart valve on said pivot projections and said central aperture of said disc occluder is engaged by said disc guide, and whereby said disc occluder pivots to a non-occluding position in response to a downstream pressure gradient across said heart valve and said central aperture of said disc occluder is engaged and guided by said cross member means and said pivot open stop means.

2. The heart valve of claim 1 wherein said disc occluder includes upstream and downstream-facing substantially flat surfaces.

3. The heart valve of claim 2 wherein said pivot open stop means includes an integral line contact surface at a predetermined angle with respect to said valve body which engages said downstream-facing surface of said disc occluder when said disc occluder is in said non-occluding position and wherein said pivot projections include surfaces at substantially said predetermined angle to said valve body that limit pivotal movement of said disc to substantially said predetermined angle with respect to said valve body in its non-occluding position.

4. The heart valve of claim 3 wherein the predetermined angle is seventy to seventy-five degrees plus or minus two degrees.

5. The prosthetic heart valve of claim 1 wherein said annular valve body includes diverging valve body inflow and outflow edges forming bell-shaped inflow and outflow sides respectively about dsaid interior wall.

6. The prosthetic heart valve of claim 5 wherein said annular valve body includes a circumferential groove recessed into and around an exterior surface of said valve body whereby said groove accepts a knitted surgical sewing ring.

7. The prosthetic heart valve of claim 1 wherein said pivot open stop means includes a substantially upstream-facing pivot open disc stop surface and said upstream-facing surface means comprises a rounded surface; and wherein said surfaces are respectively positioned about a rounded pivot surface whereby said disc occluder pivots on said rounded pivot surface and said upstream-facing pivot open disc stop surface positions said disc occluder in the non-occuluding position.

8. The prosthetic heart valve of claim 7 wherein said downstream portion of said U-shaped member is of a cross-section substantially smaller in diameter than the diameter of said center apertue of said disc occluder thereby providing downstream and upstream translation of said disc occluder in said valve body.

9. The prosthetic heart valve of claim 7 including at least one closed position disc stop having a downstream facing surface extending inward of said valve body opposite said disc guide strut means.

10. The prosthetic heart valve of claim 9 wherein said pivot projections extending inward on a chord of said valve body are equally spaced from said disc guide strut means, each of said pivot projections including a rounded pivot surface having said downstream facing disc stop surface and a pivot open stop surface positioned on respective sides of said rounded pivot surface.

11. The prosthetic heart valve of claim 10 wherein said pivot open stop surface of said pivot projections are substantially paralell in a plane to said pivot open stop surface of said disc guide strut means, and said respective planes of said pivot open stop surfaces are separated by a distance substantially equal to the thickness of said disc occluder.

12. The prosthetic heart valve of claim 10 wherein said upstream facing surface of said disc guide strut means is separated in the direction of blood flow from the plane defined by said downstream facing disc stop surfaces of said pivot projections and said downstream facing surface of said disc stop by a dimension slightly greater than the thickness of said disc occluder.

* * * * *